(12) United States Patent
D'Arpe

(10) Patent No.: US 8,505,270 B2
(45) Date of Patent: Aug. 13, 2013

(54) METHOD FOR TREATING EQUINE LAMINITIS BY CRYOTHERAPY AND AUTO-MASSAGE

(76) Inventor: Lorenzo D'Arpe, Bologna (IT)

( * ) Notice: Subject to any disclaimer, the term of this patent is extended or adjusted under 35 U.S.C. 154(b) by 89 days.

(21) Appl. No.: 12/717,973

(22) Filed: Mar. 5, 2010

(65) Prior Publication Data

US 2010/0223893 A1  Sep. 9, 2010

(30) Foreign Application Priority Data

Mar. 5, 2009 (IT) ............................... BO2009A0130

(51) Int. Cl.
*A01L 3/00* (2006.01)
(52) U.S. Cl.
USPC .................................................. 54/82; 168/2
(58) Field of Classification Search
USPC ............................ 54/82; 168/1, 2, 18, 27, 28
See application file for complete search history.

(56) References Cited

U.S. PATENT DOCUMENTS

| | | | | |
|---|---|---|---|---|
| 2,296,111 A | * | 9/1942 | Mahar | 168/28 |
| 4,444,269 A | * | 4/1984 | Laurent | 168/1 |
| 4,775,011 A | * | 10/1988 | McCuan | 168/12 |
| 4,794,991 A | * | 1/1989 | Honderich | 168/26 |
| 5,174,382 A | * | 12/1992 | Wright | 168/28 |
| 5,209,048 A | * | 5/1993 | Hanson | 54/82 |
| 5,253,715 A | * | 10/1993 | Ovnicek | 168/14 |
| 5,588,288 A | | 12/1996 | Origgi et al. | |
| 6,516,594 B2 | * | 2/2003 | Clark et al. | 54/82 |
| 6,868,656 B2 | * | 3/2005 | Osha et al. | 54/82 |
| 2006/0162296 A1 | * | 7/2006 | Maestrini | 54/82 |
| 2007/0107389 A1 | * | 5/2007 | Ruetenik | 54/82 |
| 2010/0031614 A1 | * | 2/2010 | Osborne | 54/82 |
| 2010/0095641 A1 | * | 4/2010 | Ruetenik | 54/82 |

FOREIGN PATENT DOCUMENTS

EP        0651943 A1     5/1995

OTHER PUBLICATIONS

The Steward Clog by EDSS, Inc., product abstract, retreived Sep. 25, 2112, dated Mar. 14, 2006.*
How to Construct and Apply Atraumatic Therapeutic Shoes to Treat Acute or Chronic Laminitis in the Horse in AAEP Proceedings, vol. 49, by Michael L. Steward, DVM, published in 2003.*

* cited by examiner

*Primary Examiner* — Son T Nguyen
*Assistant Examiner* — Kathleen Iwasaki
(74) *Attorney, Agent, or Firm* — Richard M. Goldberg

(57) ABSTRACT

Method and devices for treating equine laminitis by cryotherapy, comprising a boot to be fitted over the horse's hoof, having a wedge shaped sole that is angled by 20° toward the front; The purpose is accomplished by the boot in conjunction with three opportunely shaped removable soles, and a cryotherapy reservoir of flexible material, that is inserted into the boot and connected to an external device for refrigeration by circulation of a fluid.

17 Claims, 1 Drawing Sheet

METHOD FOR TREATING EQUINE LAMINITIS BY CRYOTHERAPY AND AUTO-MASSAGE

BACKGROUND OF THE INVENTION

"Equine laminitis" is known to be an inflammation of the lamellar connection between the sensitive, vascular portion, that extends along the third phalanx of the foot, and the insensitive hoof wall, resulting in their partial separation. This prevents the horse's weight from being borne by the hoof wall, transferring the load to the sole which becomes flat or convex, and to the coronary band, causing it to sink.

Laminitis generally affects the forefeet, but it is not infrequent for the hind feet to be also affected.

Its causes are not fully understood; nevertheless, because inflammation is caused by an abnormal release of histamines, the possible causes can be chiefly identified as: incorrect diet, excessive drug administration, work on very hard surfaces, untreated infections, etc.

The most evident symptoms are: shifting of weight from the front to the hind feet, lameness, heat in the hoof, incorrect gait with feet placed very far forward or very far back.

If left untreated, this pathology leads to the destruction of the dermal laminae, with consequent separation of the insensitive laminae from the sensitive laminae, starting from the anterior part of the hoof and spreading medially and laterally downward.

This process, which causes separation of the foot from the load bearing structure (hoof), produces sinking of the third phalanx (finger bone) with downward rotation of its tip, to the point of penetrating through the sole. It is clear that, if not adequately treated, laminitis can lead to loss of foot function that, in severe cases, may require euthanizing the animal.

There is thus a strong need for treatment methods capable of curing this condition.

Currently, there exist various "mechanical" types of interventions such as:
inverting the shoeing, putting the foot in a cast, application of a boot, refrigerated leg pieces, cold foot baths.

All these solutions have significant drawbacks, chiefly connected with the fact that they do not produce a full and speedy recovery, and also often require a person to continuously attend to the animal. Another known solution consists of using a rubber boot fitted over the hoof. These boots, made of natural or synthetic rubber, can be of two types. One type is a simple rubber boot worn over the shod hoof, that is used in "endurance" races to help absorb the impact on the hoof and prevent it from slipping on the terrain.

The second type of boot is fitted on the unshod hoof, and incorporates a sole angled 20° toward the front. Such boots are used for treating laminitis but with poor results, because they only keep the hoof statically in an inclined position, determined by the angle of the sole. This angle causes the "pulvinus coronae" valve to open, facilitating blood flow in the foot, but without any other beneficial effects.

Because a horse suffering from laminitis must be kept at rest inside a box, its foot does not receive the blood pumping action produced by normal walking and foot movements.

In this condition, even the application of refrigerated leg pieces produces poor results because, without the pumping action, blood stagnates in the foot without transferring the cooling to internal tissues. Furthermore, these leg pieces stop at the hoof wall, leaving uncovered precisely the part of the sole affected by the inflammation (laminitis).

FIELD OF THE INVENTION

The subject of this invention is a method for treating equine laminitis by cryotherapy, by means of a boot fitted onto the horse's hoof, which incorporates a small, flexible bladder-type reservoir, filled with a special fluid; onto the bottom of this boot there can be affixed, by means of screws, three soles, of which two with wedge shaped profile and one with convex curved profile.

The purpose of this invention is therefore to develop a method and associated devices for the treatment of laminitis.

The method consist of keeping the affected animal at rest in a box, and applying to the affected hoof a rubber boot provided with a sole that is angled forward toward the toe. The angle of this sole will be 10° for less severe cases, but can be augmented to 20° by applying a second, identically shaped sole, having an angle of 10°. This produces a total angle of 20°.

The forward inclined position of the hoof causes the "pulvinus coronae" valve to open, to a greater or lesser extent depending on the angle of the hoof, thereby restoring blood flow to the vascular part. Because the horse is kept at rest in a box, the blood pumping effect normally produced by foot movements during walking is absent.

To remedy this, an additional sole with a curved convex profile can be applied to the bottom of the boot, on the outer side, which causes the hoof to rock back and forth when placed on the ground, even with the minimal movements permitted by the standing position inside the box.

This rocking action is sufficient to alternately open and close the "pulvinus coronae" valve, as would happen during normal walking, even though the animal is confined inside a box. The normal "pumping" action of the blood in the foot is thereby restored.

To reduce the inflammation in the hoof, the boot is cooled by circulation of a refrigerated fluid stored inside a bladder (reservoir) situated in the central part of the sole, coinciding with the hoof fork.

This bladder, made from a soft synthetic material, is provided with two tubes that extend out from the boot and connect to a corresponding pair of tubes in the refrigerated leg piece, thus allowing the cooling fluid to also reach the sole of the hoof.

The blood is thus cooled by contact with the bladder and then "pumped" into circulation by the small rocking movements imparted by the boot fitted on the hoof, helping to reduce inflammation of the parts affected by laminitis (cryotherapy).

The devices of this method therefore consist of the natural or synthetic rubber boot that is fitted over the hoof, and the removable soles that can be affixed to the boot by means of screws, both of a wedge-shaped type with 10° angle, and of type with curved convex profile. The boot is moreover provided with a device for cooling the tissues, consisting of a bladder in which refrigerated fluid is circulated by external means of known type.

It is therefore apparent how the various devices of this invention work together to obtain the final result, which is the treatment of laminitis by cryotherapy.

It has in fact been experimentally ascertained that the application of the above method and its associated devices for approximately 72 hours leads to a reduction and disappearance of the pathology.

The described devices can be used in combination with each other (refrigerated boot) to administer a cryotherapy treatment, or separately (boot with wedge shaped soles) for a simple massage of the foot.

The purposes and advantages are further clarified in the description that follows and in the enclosed drawing, which schematically illustrates one possible, but not exclusive, practical embodiment of the system of this invention.

Figure 1:
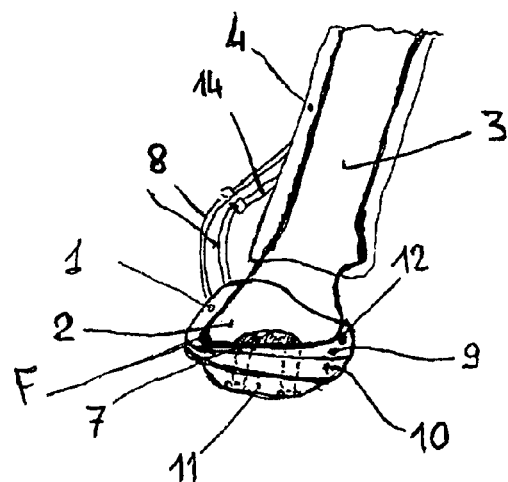
FIG. 1 shows the set of devices applied to the forefoot of a horse.
Figure 2:
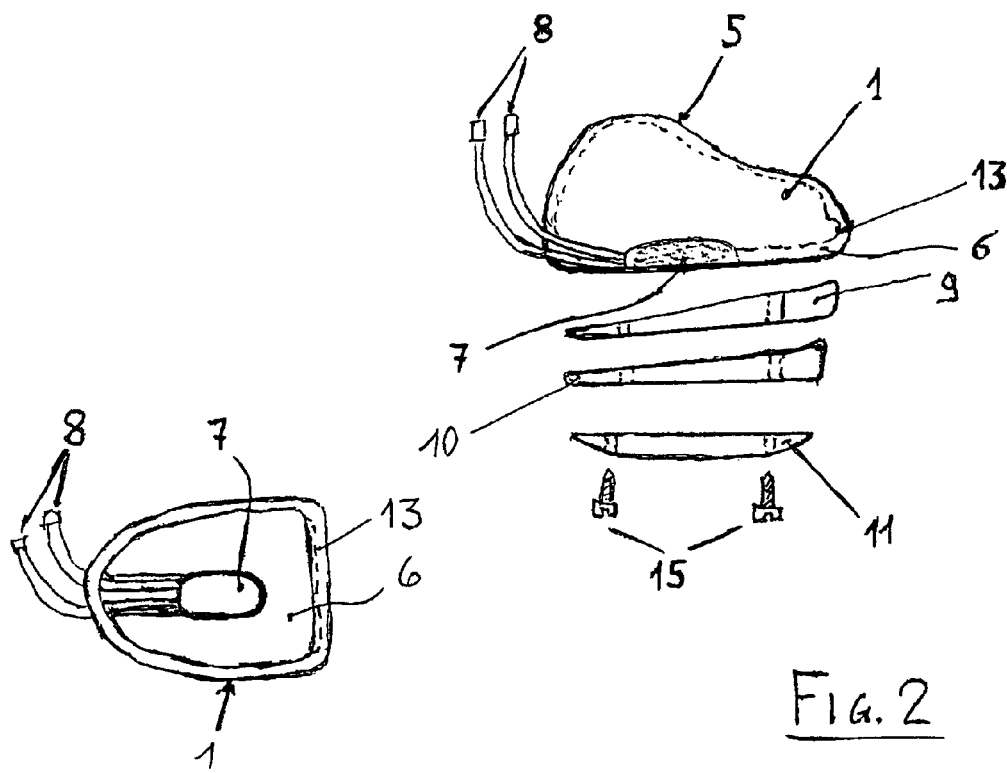
FIG. 2 shows an exploded view of the different components of the boot.
Figure 3:
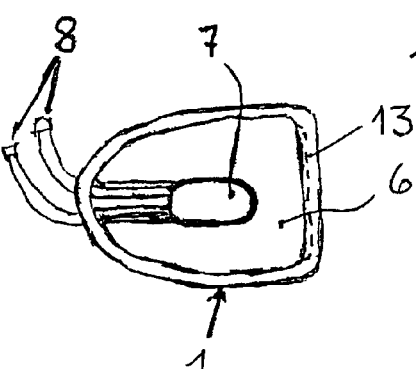
FIG. 3 shows a plan view of the boot with the inserted reservoir with tubes for connecting to the refrigerated leg piece.

The boot 1 is fitted over the hoof 2 of the horse's foot 3, to which is applied the refrigerated leg piece 4, and secured to the hoof by inserting the rear part 12 of the horseshoe F into a special recess 13 on the rear part of the boot 1.

The aforesaid boot 1 consists essentially of a hollow wrap 5 and a flat sole 6. Inserted into the thickness of sole 6, in a central position coinciding with the fork of the hoof 2, is a small reservoir 7, made of soft synthetic material, provided with two flexible tubes 8 that come out from the front of boot 1. An additional sole 9, in the shape of a wedge angled 10° from heel to toe, can be affixed to the sole 6 by means of screws 15. A second sole 10, in the shape of a wedge angled 10° from heel to toe, can be affixed to the sole 9, again by means of screws 15. By so doing, the boot 1 is inclined downward at an angle of 20° toward the toe.

A third sole 11, having a convex profile on the side towards the ground, can be affixed by means of screws 15 to the above assembly of boot 1 with soles 9 and 10.

The boot 1 can be quickly and easily fitted onto the horse's foot 3, allowing treatment to be administered with the requisite urgency, in the following way: the boot 1 is fitted directly onto the shod hoof 2, and secured in place by inserting the rear part 12 of the horseshoe F into a special recess 13 on the rear part of the boot 1.

The tubes 8 are then connected to the corresponding tubes 14 on the modified refrigerated leg piece 4.

In accordance with the veterinarian's instructions, it is then possible to add the wedge shaped soles 9 and 10, and the convex sole 11, onto the sole 6 of the boot, already fitted on the horse.

The three soles 9, 10, and 11 can be applied to the boot 1 separately or in combination. In a preferred embodiment, the first sole with 10° angle is always present, either incorporated into the structure of boot 1, or applied by means of the screws 15.

At this point the cryotherapy can begin and proceed for the required duration, without need for specialist attendance, until the inflammation disappears.

This invention, illustrated and described schematically and through examples, is also understood to embrace those accessory variants of materials and forms that, as such, fall within the scope of the following claims.

I claim:

1. A method for treating equine laminitis by auto-massage, comprising the steps of:
    providing a boot having an underside and a reservoir made of elastic material in the shape of a cryotherapy bladder,
    fitting the boot over a hoof on a horse's foot,
    providing an arrangement which angles said underside downwardly toward a front thereof at an angle up to 20°,
    providing a lowermost sole having a convex surface as a lower surface of the lowermost sole, the convex surface extending continuously over a majority of a length of the lowermost sole so that the convex surface rocks back and forth,
    applying the lowermost sole to the underside of the boot by screws such that the lower convex surface of the lowermost sole supports the boot on a ground surface, inserting the reservoir in the shape of the cryotherapy bladder into said boot such that the bladder is in direct contact with the horse's hoof, fitting a refrigerated leg piece over a horse's leg, the refrigerated leg piece having two tubes extending therefrom, inserting two tubes into the bladder of the boot, connecting the two tubes of the refrigerated leg piece to the aforesaid tubes inserted into the bladder, and connecting said leg piece to an external system for refrigeration by circulation of a non-allergenic fluid.

2. The method according to claim 1, further comprising the step of circulating the non-allergenic fluid inside the reservoir and the leg piece by the external system.

3. The method according to claim 1, further comprising the step of applying at least one of the following to the underside of the boot by the screws between the underside of the boot and the lowermost sole to provide a wedge angled downwardly toward the front thereof at said angle up to 20°:
    a first wedge shaped sole, and
    a second wedge shaped sole.

4. The method according to claim 3, wherein the first wedge shaped sole is angled at approximately 10° and comprising the step of fitting the first wedge shaped sole with an angle of 10° over the hoof while it is still shod.

5. The method according to claim 4, wherein the second wedge shaped sole is angled at approximately 10° and comprising the step of fixing the second wedge shaped sole to the first wedge shaped sole by the screws.

6. The method according to claim 5, further comprising the step of fixing the lowermost sole to one of the first and second wedge shaped soles by the screws.

7. The method according to claim 3, wherein the boot is made of one of natural and synthetic rubber, suitable for being fitted over a shod hoof; and further comprising the steps of:
    applying the first wedge shaped sole to the boot;
    applying the second wedge shaped sole to the first wedge shaped sole;
    applying the lowermost sole to the second wedge shaped sole; and
    fixing all of said soles to the underside of the boot by the screws.

8. The method according to claim 1, further comprising the step of:
    inserting said two tubes into the bladder such that said two tubes come out of a front part of the boot.

9. A device for treating equine laminitis by auto-massage, comprising:
    a boot adapted to fit over a hoof on a horse's foot, the boot including an underside, a reservoir made of elastic material in the shape of a cryotherapy bladder, and two tubes inserted into the bladder of the boot,
    an arrangement which angles said underside downwardly toward a front thereof at an angle up to 20°,
    a lowermost sole having a convex surface as a lower surface of the lowermost sole, the convex surface extending continuously over a majority of a length of the lowermost sole so that the convex surface rocks back and forth, and the lowermost sole secured to the underside of the boot by screws such that the lower convex surface of the lowermost sole supports the boot on a ground surface, and a refrigerated leg piece adapted to fit over a horse's leg, the refrigerated leg piece having two tubes extending therefrom, with the two tubes of the refrigerated leg piece adapted to be connected to the aforesaid tubes inserted into the bladder, and the refrigerated leg piece adapted to be connected to an external system for refrigeration by circulation of a non-allergenic fluid.

10. The device according to claim 9, wherein the boot includes a recess on a rear wall of the boot, and the boot is fixed to the hoof by inserting a rear part of a horseshoe into the recess on the rear wall of the boot.

11. The device according to claim 9, further comprising at least one of the following secured to the underside of the boot by the screws between the underside of the boot and the lowermost sole to provide a wedge angled downwardly toward the front thereof at said angle up to 20°:
 a first wedge shaped sole, and
 a second wedge shaped sole.

12. The device according to claim 11, wherein the first and second wedge shaped soles each have an angle of 10° from heel to toe.

13. The device according to claim 11, wherein the lowermost sole has a surface with an externally convex profile on a side thereof facing toward the ground.

14. The device according to claim 11, wherein:
 the boot is made of one of natural and synthetic rubber, suitable for being fitted over a shod hoof;
 the first wedge shaped sole is applied to the boot;
 the second wedge shaped sole is applied to the first wedge shaped sole;
 the lowermost sole is applied to the second wedge shaped sole; and
 the screws fix all of said soles to the underside of the boot.

15. The device according to claim 9, wherein the reservoir is in the shape of a soft bladder, inserted into said boot along with said two tubes inserted into the bladder such that these two tubes come out of a front part of the boot.

16. A method for treating equine laminitis by auto-massage, comprising the steps of:
 providing a boot having an underside and a reservoir made of elastic material in the shape of a cryotherapy bladder,
 fitting the boot over a hoof on a horse's foot,
 providing an arrangement which angles said underside downwardly toward a front thereof at an angle up to 20°,
 providing a lowermost sole having a convex surface as a lower surface of the lowermost sole, the convex surface extending at least along a center portion of the lowermost sole so that the convex surface rocks back and forth,
 applying the lowermost sole to the underside of the boot by screws such that the lower convex surface of the lowermost sole supports the boot on a ground surface, inserting the reservoir in the shape of the cryotherapy bladder into said boot such that the bladder is in direct contact with the horse's hoof, fitting a refrigerated leg piece over a horse's leg, the refrigerated leg piece having two tubes extending therefrom, inserting two tubes into the bladder of the boot, connecting the two tubes of the refrigerated leg piece to the aforesaid tubes inserted into the bladder, and connecting said leg piece to an external system for refrigeration by circulation of a non-allergenic fluid.

17. A device for treating equine laminitis by auto-massage, comprising:
 a boot adapted to fit over a hoof on a horse's foot, the boot including an underside, a reservoir made of elastic material in the shape of a cryotherapy bladder, and two tubes inserted into the bladder of the boot,
 an arrangement which angles said underside downwardly toward a front thereof at an angle up to 20°,
 a lowermost sole having a convex surface as a lower surface of the lowermost sole, the convex surface extending at least along a center portion of the lowermost sole so that the convex surface rocks back and forth, and the lowermost sole secured to the underside of the boot by screws such that the lower convex surface of the lowermost sole supports the boot on a ground surface, and a refrigerated leg piece adapted to fit over a horse's leg, the refrigerated leg piece having two tubes extending therefrom, with the two tubes of the refrigerated leg piece adapted to be connected to the aforesaid tubes inserted into the bladder, and the refrigerated leg piece adapted to be connected to an external system for refrigeration by circulation of a non-allergenic fluid.

\* \* \* \* \*